United States Patent [19]
Field et al.

[11] Patent Number: 5,840,763
[45] Date of Patent: Nov. 24, 1998

[54] TREATMENT OF A LATENT INFECTION OF HERPES VIRUSES

[75] Inventors: Hugh John Field; Alana Maureen Thackray, both of Cambridge; Teresa Helen Bacon, Weybridge, all of England; David Sutton, Wayne, Pa.; Richard Anthony Vere Hodge, Reigate, England

[73] Assignee: SmithKline Beecham plc, Brentford, United Kingdom

[21] Appl. No.: 522,790

[22] Filed: Sep. 1, 1995

[51] Int. Cl.$^6$ ..................................... A61K 31/52
[52] U.S. Cl. ............................. 514/262; 514/934
[58] Field of Search ...................... 514/934, 262

[56] References Cited

U.S. PATENT DOCUMENTS

| | | | |
|---|---|---|---|
| 4,355,032 | 10/1982 | Verheyden et al. | 514/934 |
| 4,423,050 | 12/1983 | Verheyden et al. | 514/934 |
| 4,461,757 | 7/1984 | Ogilvie | 514/934 |

FOREIGN PATENT DOCUMENTS

| | | | |
|---|---|---|---|
| WO 92/00742 | of 1992 | WIPO | 514/934 |

OTHER PUBLICATIONS

Physicians GenRx, pp. 808–809 (1995).
Drugs Facts & Comparisons, pp. 2252–2253 (1996).
Boyd et al., Antimicrobial Agents and Chemotherapy, 32(3), pp. 358–363 (1988).
Klein et al., Antimicrobial Agents and Chemotherapy, 27(5), pp. 763–768 (1985).
Klein et al., Antimicrobial Agents and Chemotherapy, 15(5), pp. 723–729 (1979).
Nikkels et al., Drugs, 48(4) pp. 528–548 (1994).
Drugs of the Future, 20(4), pp. 415–417 (1995).
Klein et al., Antimicrobial Agents and Chemotherapy, 24(1), pp. 129–131 (1983).
Field et al., Journal of General Virology, 56(2), pp. 259–265 (1981).

*Primary Examiner*—James H. Reamer
*Attorney, Agent, or Firm*—Dara L. Dinner; Stephen Venetianer

[57] ABSTRACT

A method for the treatment of latent infection of herpesviruses in mammals, including humans, which method comprises administering to the mammal in need of such treatment, an effective amount of a compound of formula (A):

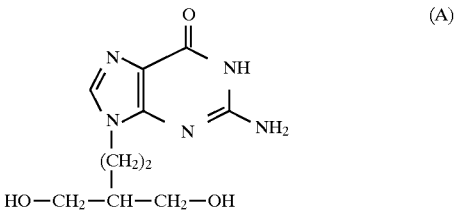

or a bioprecursor, or a pharmaceutically acceptable salt, phosphate ester and/or acyl derivative of either of the foregoing.

12 Claims, No Drawings

TREATMENT OF A LATENT INFECTION OF HERPES VIRUSES

This invention relates to treatment of latent infection of herpesviruses.

When used herein, 'treatment' includes prophylaxis as appropriate.

EP-A-141927 (Beecham Group p.l.c.) discloses penciclovir, the compound of formula (A):

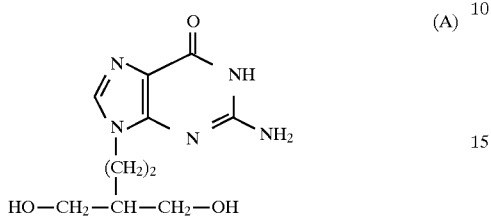

and salts, phosphate esters and acyl derivatives thereof, as antiviral agents. The sodium salt hydrate of penciclovir is disclosed in EP-A-216459 (Beecham Group p.l.c.). Penciclovir and its antiviral activity is also disclosed in Abstract P.V 11–5 p.193 of 'Abstracts of 14th Int. Congress of Microbiology', Manchester, England 7–13 September 1986 (Boyd et. al.).

Orally active bioprecursors of the compound of formula (A) are of formula (B):

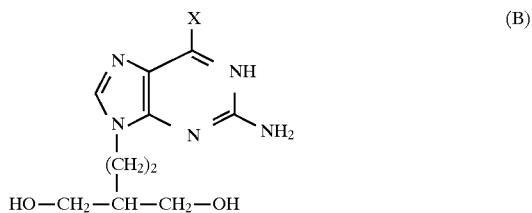

and salts and derivatives thereof as defined under formula (A); wherein X is $C_{1-6}$ alkoxy, $NH_2$ or hydrogen. The compounds of formula (B) wherein X is $C_{1-6}$ alkoxy or $NH_2$ are disclosed in EP-A-141927 and the compounds of formula (B) wherein X is hydrogen, disclosed in EP-A-182024 (Beecham Group p.l.c.) are preferred prodrugs. A particularly preferred example of a compound of formula (B) is that wherein X is hydrogen and wherein the two OH groups are in the form of the acetyl derivative, described in Example 2 of EP-A-182024, hereinafter referred to as famciclovir.

The compounds of formulae (A) and (B) and salts and derivatives thereof have been described as useful in the treatment of infections caused by herpesviruses, such as herpes simplex type 1 and herpes simplex type 2.

Previous work has shown that if antiviral treatment is delayed beyond a few hours after infection then latency is established. Once a latent infection is established, the infection can recurr.

It has now been shown in mice that famciclovir treatment can prevent the establishment of competent latency when treatment is commenced 18 h (first experiment) and up to 4 days (second experiment) after infection. It has also now been shown that latency can be prevented in an experiment in immunocompromised mice. The potential clinical advantage is that a patient, within 4 days of contact, may be treated with famciclovir to prevent not only the acute infection but also the development of latency and so avoid recurrences. Furthermore, it is thought that there may be a slow natural loss of latently infected cells and recurrent infections may be required in order to maintain the burden of latently infected cells by establishing latency in new cells. Therefore, suppressive treatment with famciclovir over a prolonged period (up to several years) may prevent new cells becoming latently infected. The result would then be curative treatment, the patient having no recurrences thereafter.

Accordingly, the present invention provides a method of treatment of latent infection of herpesviruses in humans, which method comprises the administration to the human in need of such treatment, an effective amount of a compound of formula (A):

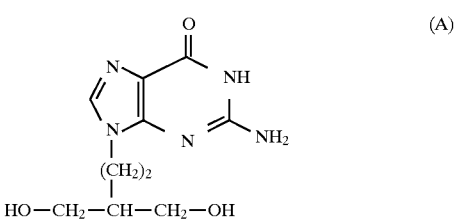

or a bioprecursor, or a pharmaceutically acceptable salt, phosphate ester and/or acyl derivative of either of the foregoing.

The term 'acyl derivative' is used herein to include any derivative of the compounds of formula (A) in which one or more acyl groups are present. Such derivatives are included as bioprecursors of the compounds of formula (A) in addition to those derivatives which are per se biologically active.

The compound of formula (A) may be in one of the forms disclosed in EP-A-216459 (Beecham Group p.l.c.).

Examples of bioprecursors, pharmaceutically acceptable salts and derivatives are as described in the aforementioned European Patent references, the subject matter of which are incorporated herein by reference.

A particular compound of formula (B) of interest is 9-(4-acetoxy-3-acetoxymethylbut-1-yl)-2-aminopurine, known as famciclovir (FCV), the well-absorbed oral form of penciclovir (PCV).

The compound of formula (A), bioprecursors, salts and derivatives may be prepared as described in the aforementioned European Patent references.

The compound, in particular, famciclovir, may be administered by the oral route to humans and may be compounded in the form of syrup, tablets or capsule. When in the form of a tablet, any pharmaceutical carrier suitable for formulating such solid compositions may be used, for example magnesium stearate, starch, lactose, glucose, rice, flour and chalk. The compound may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. Sustained release formulations, for example tablets containing an enteric coating, are also envisaged.

For parenteral administration, fluid unit dose forms are prepared containing the compound and a sterile vehicle. The compound depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

Preferred parenteral formulations include aqueous formulations using sterile water or normal saline, at a pH of around 7.4 or greater, in particular, containing penciclovir sodium salt hydrate.

As is common practice, the compositions will usually be accompanied by written or printed directions for use in the medical treatment concerned.

A suitable dosage unit might contain from 50 mg to 1 g of active ingredient, for example 100 to 500 mg. Such doses may be administered 1 to 4 times a day or more usually 2 or 3 times a day. The effective dose of compound will, in general, be in the range of from 0.2 to 40 mg per kilogram of body weight per day or, more usually, 10 to 20 mg/kg per day. in the case of famciclovir, the dosage unit would be 125 mg, 250 mg, 500 mg or 750 mg, preferably 125 mg or 250 mg.

For prevention of establishment of competent latency, the treatment is preferably carried out as soon as possible after contact with the virus, preferably within 18 hours, although up to four days is acceptable. The treatment period is usually 3 to 14 days, more usually 5 to 10 days, often 7 days.

For treatment of established recurrent disease, the treatment period is up to 5 years, for example, up to 1, 2, 3, 4, and 5 years.

The present invention also provides the use of a compound of formula (A) or a bioprecursor, or a pharmaceutically acceptable salt, phosphate ester and/or acyl derivative of either of the foregoing, in the preparation of a medicament for use in the treatment of latent infection of herpesviruses. Such treatment may be carried out in the manner as hereinbefore described.

The present invention further provides a pharmaceutical composition for use in the treatment of latent infection of herpesviruses, which comprises an effective amount of a compound of formula (A) or a bioprecursor, or a pharmaceutically acceptable salt, phosphate ester and/or acyl derivative of either of the foregoing, and a pharmaceutically acceptable carrier. Such compositions may be prepared in the manner as hereinafter described.

The compound of formula (A) and its prodrugs show a synergistic antiviral effect in conjunction with interferons; and treatment using combination products comprising these two components for sequential or concomitant administration, by the same or different routes, are therefore within the ambit of the present invention. Such products are described in EP-A-271270 (Beecham Group p.l.c.).

The following results from animal studies illustrate the invention.

EXPERIMENTS IN MICE INFECTED WITH HSV-1 VIRUS

A cutaneous infection was established by inoculation of the ear pinnae of mice with HSV-1 (SC 16) and the effects of oral famciclovir on the latent virus infection was investigated.

BALB/c female mice (Bantin and Kingman, Kingston, Hull, UK) were purchased at 3 to 4 weeks old and inoculated one week later. Virus suspension (10 ul) containing $5 \times 10^4$ p.f.u. were inoculated into the skin of the left ear pinna. Skin thickness was measured daily in individual mice by means of an Engineers'micrometre screw gauge. (ref. Nash et al, 1980, J. Gen. Virol. 48, 351–357). These mice were kept for 3 (Experiment 1) or 4 (Experiment 2) months and then killed. The trigeminal ganglia and cervical dorsal root ganglia were removed and co-cultivated. Those cultures showing virus replication were recorded as positive.

Experiment 1

In a first experiment, mice were treated within 18 h and treatment ceased on day 10 post infection.

Of the 24 untreated control mice, 12 showed latent infection in the trigeminal ganglia (TG) and 20 showed latent infection in the cervical dorsal route ganglia (DRG). All 24 control mice showed either TG or DRG latency. None of the FCV treated mice showed any latency.

Experiment 2

In a second experiment, antiviral treatment was initiated on days 1, 2, 3, 4 or 5 post-infection (p.i.) and and ceased on day 10 p.i.. The compounds were administered ad libitum in the drinking water, at 1 mg/ml (approximately 100 mg/kg/day).

The results are as shown in the following table: (Note: The groups 1 and 2 received the same treatment regimens but the results were assayed separately.)

| Antiviral Therapy (days) | Latency (Group 1) | | | | Latency (Group 2) | | | | Latency Total % Mice with virus +ve ganglia on day 120 (n = 16) L/RTG + DRG | Acute Total % Mice with virus +ve ganglia on day 8 (n = 8) L/RTG + DRG |
|---|---|---|---|---|---|---|---|---|---|---|
| | TG +ve/8 | | DRG +ve/8 | | TG +ve/8 | | DRG +ve/8 | | | |
| | Lt | Rt | Lt | Rt | Lt | Rt | Lt | Rt | | |
| None | 8 | 4 | 8 | 5 | 8 | 6 | 8 | 2 | 100 | 100 |
| 5–10 | 4 | 0 | 4 | 0 | 2 | 0 | 2 | 0 | 38 | 100 |
| 4–10 | 2 | 0 | 2 | 0 | 0 | 0 | 0 | 0 | 13 | 100 |
| 3–10 | 0 | 0 | 0 | 0 | 0 | 0 | 0 | 0 | 0 | 0 |
| 2–10 | 0 | 0 | 0 | 0 | 0 | 0 | 0 | 0 | 0 | 0 |
| 1–10 | 0 | 0 | 0 | 0 | 0 | 0 | 0 | 0 | 0 | 0 |

TG = trigeminal
DRG = dorsal root ganglia
L/R = left/right

Similar results were obtained when compounds were administered twice daily by gavage at 50 mg/kg per dose. Four months later, latent virus could be reactivated in ganglia explants (ipsilateral and contralateral trigeminal and dorsal root) from all of 16 control mice. Latent virus was not reactivated from the ganglia of FCV-treated mice, except ipsilateral ganglia, and only when the start of therapy was delayed until days 4 p.i. (2/16) or 5 p.i (6/16).

Experiment 3

Mice were treated with Cyclosporin A (CyA) from day −2 to day=10 (day 0 being the day of infection). Groups of mice were untreated (control), or treated with famciclovir orally at 50 mg/kg twice daily from 22h after infection to 5.5 or 10.5 days. The ganglia were examined for reactivation of infectious virus 1 or 4 months later and the results are shown in the Table below.

|         | LTG (n = 6) | RTG (n = 6) | LDR (n = 6) | RDR (n = 6) |
|---------|-------------|-------------|-------------|-------------|
| Control | 6           | 4           | 6           | 3           |
| FCV     | 0           | 0           | 0           | 0           |

EXPERIMENTS IN MICE INFECTED WITH HSV-2 VIRUS

A cutaneous infection was established by inoculation of the ear pinnae of mice with HSV-2 and the effects of oral famciclovir on the latent virus infection was investigated. Treatment was 50 mg/kg twice daily for 5 days starting 22 h post-infection.

The table shows the number of mice/group with positive latent infection in the trigeminal or cervical dorsal root ganglia.

| Group | No. of mice with +ve ganglia number of mice tested | | | | % mice |
|-------|------|------|------|------|------|
|       | Left T/G | Right T/G | Left CDR | Right CDR | yielding at least one +ve ganglion |
| Control | 10/10 | 10/10 | 10/10 | 6/10 | 100 |
| famciclovir | 0/10 | 0/10 | 0/10 | 0/10 | 0 |

What we claim is:

1. A method for reducing reactivation of a latent infection of herpes viruses in a human in need thereof which method comprises administering to said human an effective amount of famciclovir, or penciclovir, or a pharmaceutically acceptable salt thereof, at greater than 18 hours post-infection.

2. A method according to claim 1 wherein the treatment is for latent infection of herpes simplex type 1 infection.

3. A method according to claim 1 wherein the treatment is for latent infection of herpes simplex type 2 infection.

4. A method according to claim 1 wherein famciclovir is administered at a dose of 125 mg, 250 mg, 500 mg, 750 mg, or 1 g, once, twice or three times a day.

5. The method according to claim 1 wherein the time of administration is four (4) days or greater post-infection.

6. The method according to claim 1 wherein the length of time for reduction of the latent herpes viruses is from 3 to 14 days.

7. A method for the reducing the amount of, or eliminating the establishment of, a latent infection of herpes viruses in a human in need thereof which method comprises administering to said human an effective amount of famciclovir, or penciclovir, or a pharmaceutically acceptable salt thereof, at greater than 18 hours post-infection.

8. The method according to claim 7 wherein the latent herpes viral infection is HSV-1.

9. The method according to claim 7 wherein the latent herpes viral infection is HSV-2.

10. The method according to claim 7 wherein famciclovir is administered at a dose of 125 mg, 250 mg, 500 mg, 750 mg, or 1 g, once, twice or three times a day.

11. The method according to claim 7 wherein the time of administration is four (4) days or greater post-infection.

12. The method according to claim 7 wherein the length of time for reduction of the latent herpes viruses is from 3 to 14 days.

\* \* \* \* \*